United States Patent [19]

Mansuripur et al.

[11] Patent Number: 5,108,185

[45] Date of Patent: * Apr. 28, 1992

[54] APPARATUS FOR MEASURING REFLECTIVITY

[75] Inventors: Masud Mansuripur, Newton Highlands; Michael Ruane, Brookline; Robert Rosenvold, Brighton, all of Mass.

[73] Assignee: Boston University, Boston, Mass.

[*] Notice: The portion of the term of this patent subsequent to Jun. 13, 2006 has been disclaimed.

[21] Appl. No.: 365,172

[22] Filed: Jun. 12, 1989

Related U.S. Application Data

[63] Continuation of Ser. No. 61,886, Jun. 12, 1987, Pat. No. 4,838,695.

[51] Int. Cl.$^5$ .............................................. G01J 4/04
[52] U.S. Cl. ................................................... 356/369
[58] Field of Search ........................................ 356/369

[56] References Cited

U.S. PATENT DOCUMENTS

| | | |
|---|---|---|
| 3,155,944 | 11/1964 | Oberg et al. |
| 3,445,833 | 5/1969 | Lins |
| 3,451,740 | 6/1969 | Smith |
| 3,512,866 | 5/1970 | Griffiths et al. |
| 3,516,747 | 6/1970 | Moore |
| 3,734,625 | 5/1973 | Aagard |
| 4,050,895 | 9/1977 | Hardy et al. |
| 4,210,401 | 7/1980 | Batten |
| 4,265,543 | 5/1981 | Barclay et al. |
| 4,585,348 | 4/1986 | Chastang et al. |
| 4,692,024 | 9/1987 | Bloss |

OTHER PUBLICATIONS

Harrison et al., "A High Frequency Kerr-Effect Microscope for Bubble Devices", *IEEE Transactions on Instrumentation and Measurement*, vol. IM-30, No. 3 (Sep. 1981), pp. 202-205.

Moy, J. P., "Immersion ellipsometry", *Applied Optics*, vol. 20, No. 22 (Nov. 15, 1981), pp. 3821-3822.

Ruiz-Urbieta et al., "Methods for Determining Film Thickness and Optical Constants . . . ", *Journal of the Optical Society of America*, vol. 61, No. 3 (Mar. 1971), pp. 351-359.

Mansuripur et al., "Signal and Noise in Magneto-Optical Readout", *Journal of Applied Physics*, vol. 53, No. 6 (Jun. 1982), pp. 4485-4494.

*Applied Optics*, 25, No. 12, Ruane et al., "Measurement of Reflectivities for Magnetooptical Media", Jun. 15, 1986, pp. 1946-1951.

Ruane et al., "Dielectric Tensor Characterization of Overcoated Amorphous TbFe Alloys", pp. 1-8, no date.

*Applied Optics*, 25, No. 22, Sprokel, "Photoelastic Modulated Ellipsometry on Magnetooptic Multilayer Films", Nov. 15, 1986, pp. 4017-4022.

*Applied Optics*, 23, No. 22, Sprokel, "Reflectivity, Rotation, and Ellipticity of Magnetooptic Film Structures", Nov. 15, 1984, pp. 3983-3989.

*Ind. Eng. Chem. Prod. Res. Dev.*, 24, Mansuripur et al., "Erasable Optical Disks for Data Storage: Principles and Applications", 1985, pp. 80-84 (no month).

*Proceedings*, Chen et al., "Thickness Dependence of Magnetooptic Effects in Terbium-Iron Films", Jan. 17-20, 1983, pp. 260-263.

*SPIE*, 420, Mansuripur and Connell, "Magneto-optical Recording", 1983, pp. 222-230 (no month).

*J. Appl. Phys.*, 60, No. 1, Wolniansky et al., "Magneto-optical Measurements of Hysteresis Loop and Anisotropy Energy Constants on Amorphous $Tb_xFe_{1-x}$ Alloys", Jul. 1, 1986, pp. 346-351.

(List continued on next page.)

Primary Examiner—Richard A. Rosenberger
Attorney, Agent, or Firm—Hamilton, Brook, Smith & Reynolds

[57] ABSTRACT

An apparatus for measuring the reflectivity of magnetooptic materials where the complex reflection coefficients of absorbing anisotropic media are determined. Amorphous rare-earth transition metal alloys exhibiting polar Kerr effect are analyzed for use as storage media in erasable optical storage systems.

16 Claims, 6 Drawing Sheets

OTHER PUBLICATIONS

*Appl. Phys. Lett.*, 49, No. 1, Mansuripur, "Figure of Merit for Magneto-optical Media Based on the Dielectric Tensor", Jul. 7, 1986, pp. 19-21.

*J. Appl. Phys.*, 52, No. 11, Theeten et al., "Nondestructive Analysis of $Si_3N_4/SiO_2/Si$ Structures Using Spectroscopic Ellipsometry", Nov. 1981, pp. 6788-6797.

*Applied Optics*, 14, No. 1, Aspnes and Studna, "High Precision Scanning Ellipsometer", Jan. 1975, pp. 220-228.

*Institute for Armorphous Studies Series*, Connell and Bloomberg, "Amorphous Rare-Earth Transition-Metal Alloys", pp. 739-752 (no date).

*Handbook of Optics*, Driscoll (Editor), pp. 10-6 to 10-30 (no date).

*IBM Technical Disclosure Bulletin*, 1, No. 5, Hart, "Magnetooptic Hysteresigraph", Feb. 1959, pp. 18-19.

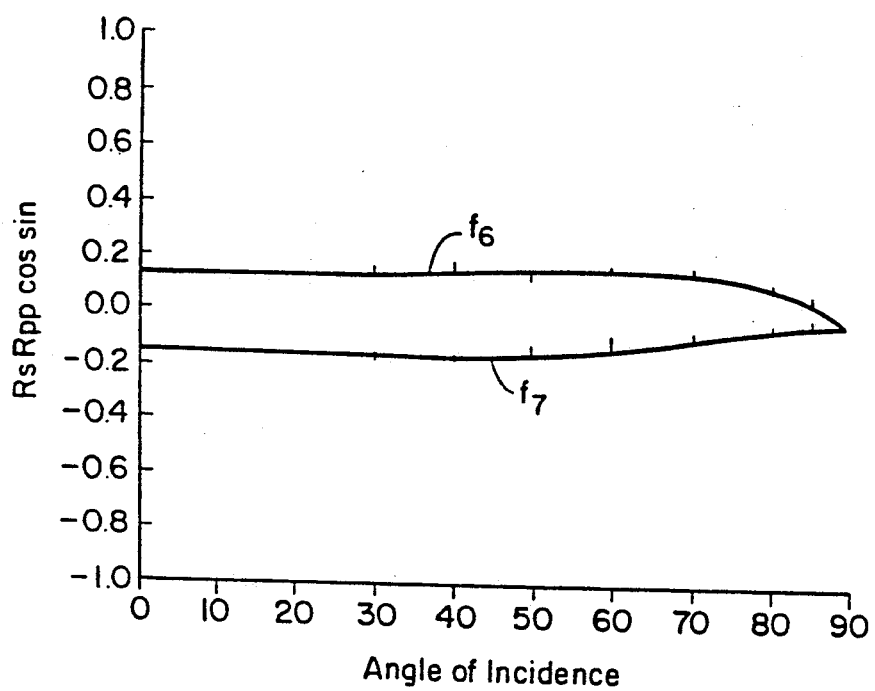

APPARATUS FOR MEASURING REFLECTIVITY

This application is a continuation of U.S. Ser. No. 07/061,886 filed Jun. 12, 1987, now U.S. Pat. No. 4,838,695 issued Jun. 13, 1989.

BACKGROUND OF THE INVENTION

Amorphous rare earth-transition metal alloys (RE-TM) can possess strong perpendicular anisotropy and exhibit polar Kerr effect when prepared as thin films with appropriate compositions. This property makes RE-TM films good candidates for storage media in erasable optical storage systems using thermomagnetic writing and magnetooptical readout. See P. Chaudhari, N. J. Cuomo, and R. J. Gambino, "Amorphous Metallic Films for Magneto-Optic Applications," Appl. Phys. Lett. 22, 337 (1973). R. P. Freese, R. N. Gardner, T. A. Rinehart, D. W. Siitari, and L. H. Johnson, "An Environmentally Stable, High Performance, High Data Rate Magneto-Optic Media," Proc. Soc. Photo-Opt. Instrum. Eng. 529,6 (1985).

Reflection of light falling at oblique incidence on the boundary between two media of different refractive indices is usually described by two Fresnel amplitude reflection coefficients $r^p$ (for incident p-polarized light) and $r^s$ (for incident s-polarization). These are real numbers for nonabsorbing isotropic media. For absorbing media, there is both a magnitude and phase change in the reflected light, so that the reflection coefficients are complex. G. A. N. Connell and D. S. Bloomberg, Mott Festschrift, Plenum, N.Y. (1985). RE-TM magnetooptical media are both absorbing and anisotropic, so that their $r^p$ and $r^s$ are complex; in addition, they possess a third complex reflection coefficient r that describes optical activity in terms of the coupling of incident p- or s- polarized light into the orthogonal polarized components of the light after reflection.

A number of traditional ellipsometric methods have been used to partially characterize optical properties of films. J. Bennett, H. Bennett, "Polarization," in *Handbook of Optics* (McGraw-Hill, New York, 1978), and R. M. A. Azzam and N. M. Bashara *Ellipsometry and Polarized Light* (North-Holland, N.Y., 1977). Ellipsometry measured the reflection of polarized light striking a material at oblique incidence by nulling the reflected signal with an analyzer. These measurements describe reflecting properties in terms of the relative phase change $\Delta = \phi^p - \phi^s$, and the relative amplitude attenuation, $\tan\gamma = |r^p|/|r^2|$, that are introduced by reflection from the material. From these quantities other properties, most often surface film thickness and optical constants can be determined. Recent attempts to extend ellipsometry have used $\Delta$ and $\tan\gamma$ to obtain the off-diagonal elements of the dielectric tensor. See G. J. Sprokel, "Reflectivity, Rotation, and Ellipticity of Magnetooptic Film Structures." Appl. Opt. 23, 3983 (1984) and G. J. Sprokel, "Photoelastic Modulated Ellipsometry on Magnetooptic Multilayer Films," Appl. Opt. 25, 4017 (1986).

U.S. Pat. No. 3,155,944 discloses use of polarized light to read a magnetically recorded thin film. Polarized light reflected from the film and rotated by the Kerr effect is passed through an analyzer which is rotated for near extinction of the reflected light when the film is magnetized in one stable state. With the analyzer held fixed in this position, when the remanent state of the film is switched by applying a suitable field, the plane of polarization of the reflected light will be rotated resulting in a substantial increase in light intensity.

SUMMARY OF THE INVENTION

The present invention utilizes a polarized light source to illuminate a magnetooptic material so as to measure its reflective characteristics. Two detectors are mounted so as to measure the orthogonal components of the electric field intensity of the reflected polarized light. One measures the parallel component of the signal, and the other the perpendicular component.

In a preferred embodiment, the magnetooptic material is covered by a transparent protective layer to avoid any degradation of the material's surface. Due to reflection and refraction of light by the protective layer an additional lens is interposed between the layer and the light source. One embodiment utilizes a hemispherical lens having an index of refraction matching that of the protective layer. Light incident from various angles upon the magnetooptic material and its protective layer always enters the lens at a right angle. A film is placed between the lens and layer having essentially the same index of refraction as both the lens and layer so that light transmitted through the lens, the film, and the layer is not refracted or reflected prior to reaching the magnetooptic surface. Any losses due to the optics of the system can be calculated by removing the sample to allow total internal reflection by the lens. The measured signals can then be normalized by this totally reflected light.

A preferred embodiment utilizes a pulsed electromagnet to reverse the direction of magnetization of the material. This permits sign reversal of the reflection coefficient $r_\perp$, while leaving other parameters intact.

The apparatus permits the calculation of the complex reflection coefficients of light absorbing, anisotropic and magnetooptic media. These values can be determined as a function of the angle of incidence of the polarized light on the magnetooptic material. The orientation of polarization of both the incident light and the reflected light can be adjusted.

An adjustable phase delay can be introduced between the reflected parallel and perpendicular polarization components. The phase delay is determined so as to create independent observations of the magnitudes and phases of the complex reflection coefficients.

BRIEF DESCRIPTION OF THE DRAWINGS

FIGS. 5(a)-5(c) are a graphical comparison of theoretical and averaged experimental values for TbFeAr.

DETAILED DESCRIPTION OF THE INVENTION

Figure 1:
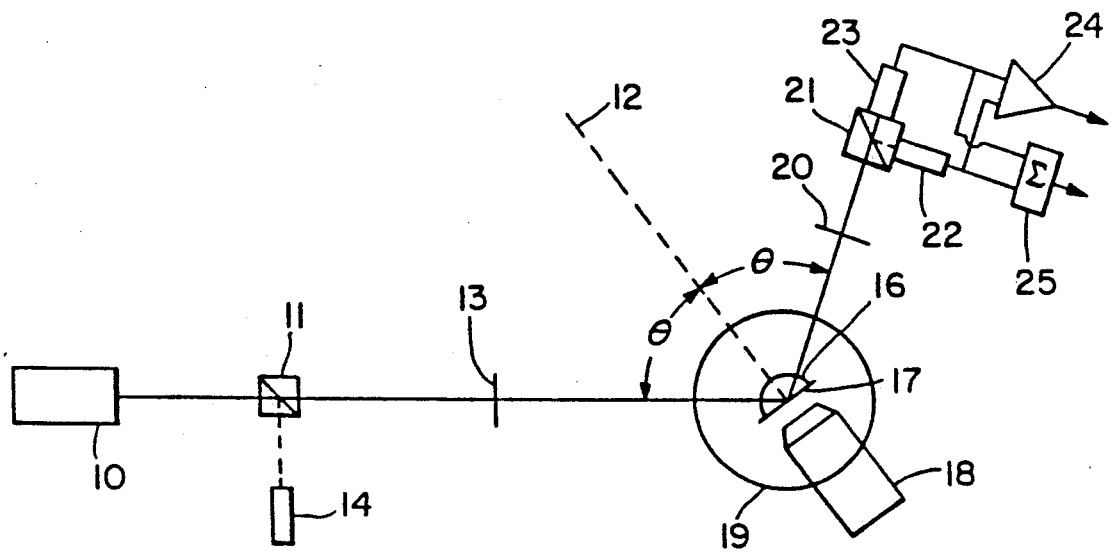
FIG. 1 is a schematic illustration of the apparatus for measuring reflectivity.

Apparatus for measuring reflectivity is illustrated in FIG. 1. A linearly polarized HeNe laser is used as a light source 10. The beam is incident on a polarizing beam splitter 11, which splits the beam into p- and s-polarized components. One component proceeds to detector 14, which is used to measure variations of the light source 10 and to normalize the output to account for these variations. The detector 14 may be rotatably attached to the beam splitter 11. Before the beam splitter 11 the laser signal is linearly polarized at an angle of 45° to the plane of the figure. The polarization vector may be rotated by rotating the beam splitter 11. The axis of the beam splitter 11 has angle $\beta$ with the plane of reference, and thus the polarization vector that is incident on the sample has angle $\beta$. Lens 13 is a long focal length lens that focuses the beam on the sample through hemispherical lens 16.

The sample 17 is assumed to have a transparent overcoat layer over an optically thick film of magnetooptic material. Lens 16 allows the beam to strike the magnetic film directly at all angles of incidence without being bent by the glass overcoating layer. It also reduces reflection of the incident beam at the air-overcoat boundary and trapping by internal reflection of the reflected beam as it leaves the overcoating layer. This is because the beam always enters and leaves lens 16 normally (the overcoating is negligible compared with lens 16 dimensions) and because lens 16, the index matching oil, and overcoating have the same index of refraction n.

An electromagnet 18 is used to reverse the direction of polarization of the magnetooptic material of sample 17. A pulsed electromagnet 18 can produce a field of up to 7 kOe perpendicular to the sample, and its position is such that the illuminated area of the sample always receives the strongest field. The magnet 18, sample 17, and hemispherical lens 16 are all mounted on a rotatable base 19, which pivots around an axis perpendicular to the plane in FIG. 1. The axis passes through the plane of the sample and the center of the hemispherical lens. In a preferred embodiment, the angle of incidence, $\theta$, as measured from the normal 12 from sample 17, can be varied from a minimum of 15° to a maximum of 88°.

The reflected beam goes through a $\frac{1}{4}$ wave plate, 20, which, as will be shown below, will help identify the phase difference between the reflected components of polarization. The fast axis of the $\frac{1}{4}$ wave plate 20 has angle $\zeta$ with the reference plane.

In a preferred embodiment, the beam splitter 21 and detectors 22 and 23 may be rotated by an angle $\eta$. Beam splitter 21 splits the reflected beam into two components and directs these two components into the detectors 22 and 23 respectively. Alternatively, a $\frac{1}{2}$ wave plate rotates the polarization with respect to the polarizing beam splitter whose transmission axis is parallel to the plane of reference. The angle of the fast axis of the $\frac{1}{2}$ wave plate would then be noted by $\eta/2$. The two photodetectors 22 and 23 are identical, and their conversion factor, defined as the ratio of the output voltage to the input light intensity is $\alpha$. We will denote the individual detector outputs by $S_1$ and $S_2$. Means for adding these two signals 25 is shown in FIG. 1 with the sum designated by $\sigma$. The difference between the two signals appears at the output of the electronic differential amplifier 24, and is designated by $\Delta S$.

Figure 2:
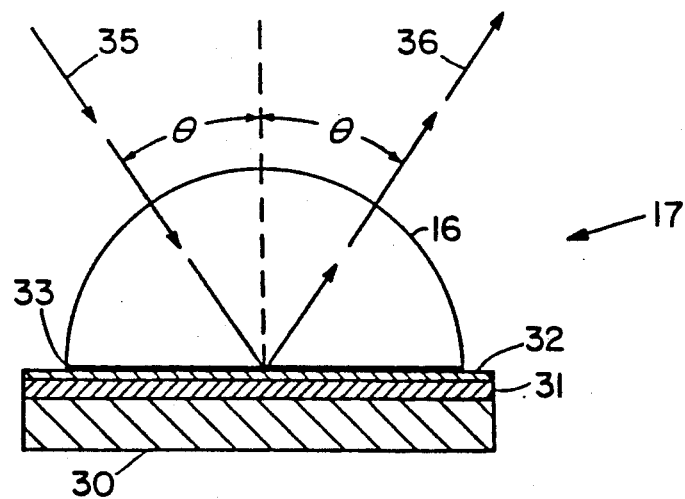
FIG. 2 is a cross-sectional view of the configuration of the magnetooptic material, layer, film, and lens.

FIG. 2 shows a cross section of a typical configuration of the sample 17 with the lens 16. Magnetooptic material 31 is deposited on a quartz substrate 30. A transparent protective layer 32 is then deposited onto the material 31. Hemispheric lens 16 is then placed on top of the layer 32 with a thin film matching oil 33 interposed between them. The refractive index of the film 33 matches the refractive indices of the hemispherical lens 16 and the protective layer 32. This is to insure that light being transmitted through the lens, film and layer is not refracted or reflected at any of these interfaces.

To normalize the measurement results, we must know the effective light amplitude that goes through the system. This can be measured by removing the sample and allowing the light to undergo total internal reflection at the back surface of the hemispherical lens. The angle of incidence, $\theta$, must be larger than the critical angle (approximately 42°), but the orientation of the phase plates is arbitrary. If the effective light amplitude is denoted A the sum of the signals $S_1$ and $S_2$ will be given by $\sigma_0 = S_1 + S_2 = \frac{1}{2}(\alpha)A^2$. In the following discussion, we will assume that the results are normalized by $\sigma_0$.

The experimental results obtained from the above apparatus may be compared with a theoretical characterization. The dielectric tensor for magnetooptical media of interest can be written as $$e = \begin{pmatrix} e_x & ie_{xy} & 0 \\ -ie_{xy} & e_y & 0 \\ 0 & 0 & e_z \end{pmatrix} \quad (1)$$

Where a coordinate system is chosen so that the plane of the film is x-y, and the magnetization direction z. The films are amorphous and isotropic in the x-y plane. Thus $e_x = e_y$. Since the films are grown in the z-direction, there may be some kind of growth-induced anisotropy in this direction, such as columnar structure. We, therefore, allow $e_z$ to be different from $e_x$ and $e_y$.

Let a plane monochromatic wave propagate in this medium along the unit vector $S = (S_x, S_y, S_z)$. From symmetry, one can set $S_y = 0$ without loss of generality; thus $S_x^2 + S_z^2 = 1$. In general, the electromagnetic quantities $\vec{E}$, $\vec{D}$, $\vec{H}$, and $\vec{B}$ have the following form:

$$\vec{V}(r,t) = \vec{V}_0 \exp(i[(2\pi n/\lambda_0)\vec{S}\cdot\vec{r} - wt]) \quad (2)$$

$\vec{r}$ is the position vector, $\omega = 2\pi f$ is the frequency of the electromagnetic disturbance, $\lambda_0 = c/f$ is the vacuum wavelength, and n is the refractive index of the medium to be determined below. From Maxwell's equations $$\vec{\nabla} \times \vec{E} = -\frac{1}{c} \frac{\partial \vec{B}}{\partial t} \quad (3a)$$

$$\vec{\nabla} \times \vec{H} = \frac{1}{c} \frac{\partial \vec{D}}{\partial t} \quad (3b)$$

where $\vec{B} = \mu \vec{H}$. At the optical frequencies $\mu = 1$, and we can write $$\vec{\nabla} \times \vec{\nabla} \times \vec{E} = \frac{\omega^2}{c^2} \vec{D}.$$

Replacing for $\vec{E}$ and $\vec{D}$ from Eq. (2) we arrive at $$n^2[\vec{E}_0 - (\vec{S}\cdot\vec{E}_0)\vec{S}] = \vec{D}_0 \quad (5)$$

Now $\vec{D}_0 = e\vec{E}_0$, and, therefore, $$\begin{pmatrix} e_x - n^2 S_z^2 & ie_{xy} & n^2 S_x S_z \\ -ie_{xy} & e_x - n^2 & 0 \\ n^2 S_x S_z & 0 & e_z - n^2 S_x^2 \end{pmatrix} \begin{pmatrix} E_{x0} \\ E_{y0} \\ E_{z0} \end{pmatrix} = 0 \quad (6)$$

Equation (6) will have a nontrivial solution if and only if the determinant of the matrix is equal to zero. This yields the following fourth-order equation in n:

$$(e_x S_x^2 + e_z S_z^2)n^4 - [(e_x^2 - e_{xy}^2) S_x^2 + e_x e_z(1 + S_z^2)]n^2 + e_z(e_x^2 - e_{xy}^2) = 0 \quad (7)$$

In general, there will be two solutions, $n_1$ and $n_2$, for the medium specified by the dielectric matrix of Eq. (1). Once n is replaced in Eq. (6) the $\vec{E}$ vector will be determined within a multiplicative constant. The magnetic field vector $\vec{H}$ can also be obtained in terms of $\vec{E}$. Replacing for $\vec{E}$ and $\vec{B}$ in Eq. (3a) from Eq. (2) and setting $\mu = 1$ we obtain $$\vec{H}_0 = n(\vec{S} \times \vec{E}_0) \quad (8)$$

Let us now consider the interface of our magnetooptic medium with a homogeneous medium of refractive index $n_0$. The interface is the plane $z=0$, and the beam is incident from the isotropic medium at an angle $\theta$, as shown in FIG. 2. The continuity of the tangential components of $\vec{E}$ and $\vec{H}$ at the interface requires that the reflected beam and both refracted components remain in the x-y plane. Moreover, the reflected beam will have the same angle $\theta$ with the normal as the incident beam and (Snell's law);

$$n_0 \sin\theta = n_1 S_{x1} = n_2 S_{x2} \quad (9)$$

Replacing $nS_x$ with $n_0\sin\theta$ in Equation (7) and solving for n yield $$n^2 = e_x + \frac{1}{2}\left(1 - \frac{e_x}{e_z}\right)n_0^2\sin^2\theta \pm \left[\left[\frac{1}{2}\left(1 - \frac{e_x}{e_z}\right)n_0^2\sin^2\theta\right]^2 + \left(1 - \frac{n_0^2\sin^2\theta}{e_z}\right)e_{xy}^2\right]^{\frac{1}{2}}. \quad (10)$$

From this equation we can obtain the refractive indicies, $n_1$ and $n_2$, for the two refracted beams in terms of the dielectric tensor elements and the angle of incidence $\theta$. Once $n_1$ and $n_2$ are determined, we resolve the incident $\vec{E}$ field into its parallel and perpendicular components $E_p^{(i)}$ and $E_x^{(i)}$, respectively. The continuity of $E_x$, $E_y$, $H_x$, and $H_y$ at the interface gives rise to four equations in the four unknowns $E_p^{(r)}$, $E_s^{(r)}$, $E^{(t1)}$, and $E^{(t2)}$. $E^{(t1)}$, and $E^{(t2)}$ are the magnitudes of the two E field vectors in the magnetooptical medium, while $E_p^{(r)}$ and $E_s^{(r)}$ refer to the parallel and perpendicular components of the reflected beam, respectively. To express the solutions in compact form, let us define the following parameters:

$$a_i = (n_i/n_0)^2 - \frac{e_x}{n_0^2} \quad i = 1,2; \quad (11a)$$

-continued
$$b_i = [(n_i/n_0)^2 + [(n_i/n_0)^2 - 1]\tan^2\theta]^{\frac{1}{2}} \quad i = 1,2; \quad (11b)$$

$$c = 1 + \left(1 - \frac{n_0}{e_z}\right)\tan^2\theta \quad (11c)$$

Then, when $E_s^{(i)} = 0$, we have $$r^{(p)} = \frac{E_p^{(r)}}{E_p^{(i)}} = \frac{a_1(c - b_1)(1 + b_2) - a_2(c - b_2)(1 + b_1)}{a_1(c + b_1)(1 + b_2) - a_2(c + b_2)(1 + b_1)} \quad (12)$$

$$r_\perp^{(p)} = \frac{E_s^{(r)}}{E_p^{(i)}} = \frac{2ic(b_1 - b_2)(e_{xy}/n_0^2)\cos\theta}{a_1(c + b_1)(1 + b_2) - a_2(c + b_2)(1 + b_1)} \quad (13)$$

Similarly, when $E_p^{(i)} = 0$, we have $$r^{(s)} = \frac{E_s^{(r)}}{E_s^{(i)}} = \frac{a_1(c + b_1)(1 - b_2) - a_2(c + b_2)(1 - b_1)}{a_1(c + b_1)(1 + b_2) - a_2(c + b_2)(1 + b_1)} \quad (14)$$

$$r_\perp^{(s)} = \frac{E_p^{(r)}}{E_s^{(i)}} = \frac{2\,ia_1a_2(b_1 - b_2)(n_0^2/e_{xy})(1/\cos\theta)}{a_1(c + b_1)(1 + b_2) - a_2(c + b_2)(1 + b_1)}. \quad (15)$$

Figure 3A:
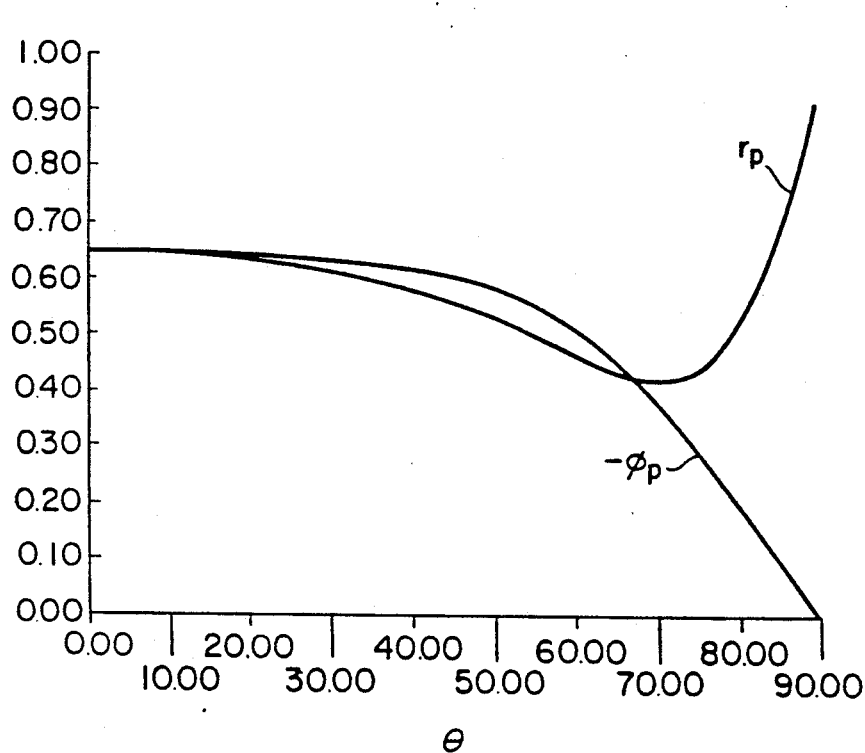
FIGS. 3(a)-3(c) graphically depict theoretical values for the reflection coefficients of $Tb_{28} Fe_{72}$.
Figure 3B:
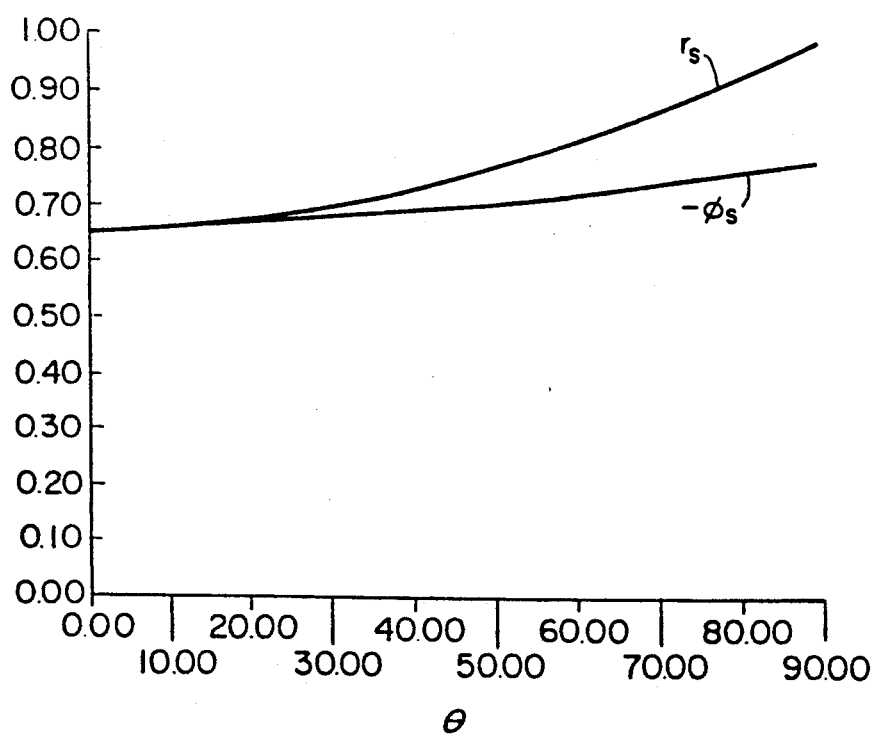
Figure 3C:
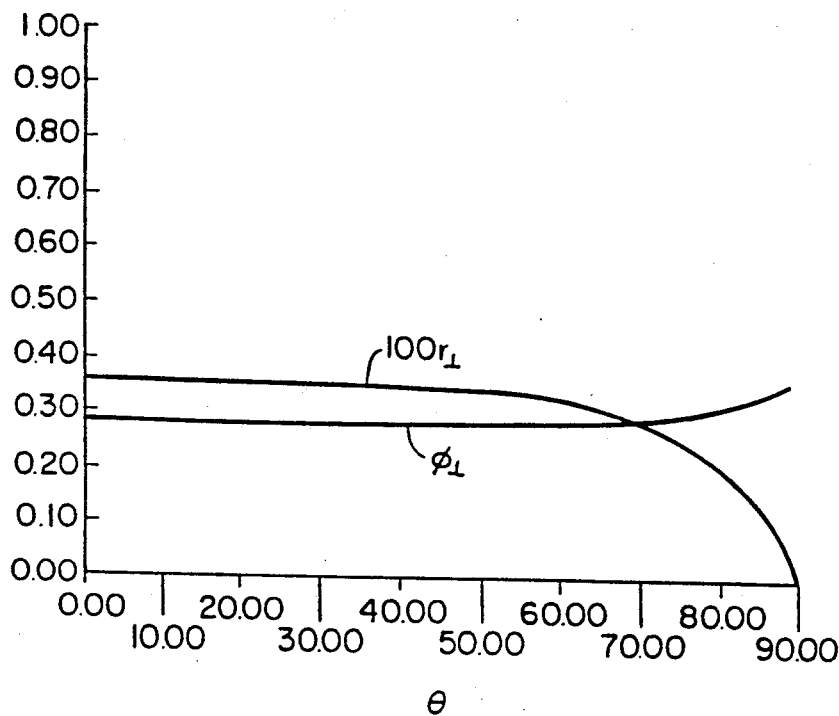

Using Eqs. (10) and (11) in Eqs. (13) and (15) it is possible to show that $$r_{195}^{(p)} = -r_\perp^{(s)} \quad (16)$$

which is intuitively reasonable given the physical nature of the magnetooptical interaction. Also notice that when the magnetization is switched the sign of $e_{xy}$ is reversed. This results in a sign reversal for $r_\perp$ but leaves other parameters intact. FIG. 3 shows the complex reflectivities $r^{(p)}$, $r^{(s)}$, and r for a typical magnetooptical medium. The dielectric tensor elements are $e_x = e_z = -2.6 + i(20.0)$, $e_{xy} = -0.04 + i(0.33)$, and the medium of incidence is glass ($n_0 = 1.5$). Note that in FIG. 3(c), the magnitude and phase of $r_\perp$ remain constant until nearly 60°. In many magnetooptical readout systems, high numerical aperture lenses are used, and incident rays far from the center of the lens can strike the medium at angles as high as 40° or 50°. FIG. 3(c) shows that the reflectivity $r_\perp$, which determines the strength of the signal, is nearly constant for all the rays through such a lens.

When the sample is placed in the system the signals, $S_1$ and $S_2$, will in general depend on $r^{(p)}$, $r^{(s)}$, and $r_\perp$ as well as on $\beta$, $\zeta$, and $\eta$.

For simplicity of notation let us define $$r^{(p)} = r_p \exp(i\phi_p)$$

$$r^{(s)} = r_s \exp(i\phi_s)$$

$$r_\perp = r_\perp \exp(i\phi_\perp) \quad (17)$$

Then, after some straightforward but tedious calculations, we will obtain $$\sigma/\sigma_0 = r_p^2 \cos^2 2\beta + r_s^2 \sin^2 2\beta + r_\perp^2 + [r_p r_\perp \cos(\phi_p - \phi_\perp) - r_s r_\perp \cos(\phi_s - \phi_\perp)]\sin 4\beta$$

$$\Delta S/\sigma_0 = [(r_p{}^2 \cos^2 2\beta - r_s{}^2 \sin^2 2\beta) \cos 2\zeta - r_\perp{}^2$$
$$\cos(4\beta - 2\zeta)] \cos(4\eta - 2\zeta) + r_p r_s [\sin 2\zeta \cos(\phi_p - \phi_s)$$
$$\cos(4\eta - 2\zeta) + \sin(\phi_p - \phi_s) \sin(4\eta - 2\zeta)]$$
$$\sin 4\beta - 2r_p r_\perp [\cos 2\beta \sin(\phi_p - \phi_\perp) \sin(4\eta - 2\zeta) +$$
$$\sin(2\zeta - 2\beta) \cos(\phi_p - \phi_\perp) \cos(4\eta - 2\zeta)]$$
$$\cos 2\beta - 2r_s r_\perp [\sin 2\beta \sin(\phi_s - \phi_\perp)$$
$$\sin(4\eta - 2\zeta) - \cos(2\zeta - 2\beta) \cos(\phi_s - \phi_{195})$$
$$\cos(4\eta - 2\eta)] \sin 2\beta \qquad (18)$$

By selecting certain values for the angles $\beta$ and $\zeta$ the significance of this expression can be illustrated. Specifically, the reflection coefficients $r_p$, $r_s$, and $r_\perp$, can be determined from the output signals $S_1$ and $S_2$. Assuming a $\lambda/2$ plate is used to rotate polarization consider the following experiments:

Experiment 1: Set $\beta = 0$. Then $$\sigma/\sigma_0 = r_p{}^2 + r_\perp{}^2 \approx r_p{}^2 \qquad (19)$$

Next set $\beta = 45°$. Then $$\sigma/\sigma_0 = r_s{}^2 + r_\perp{}^2 \approx r_s{}^2 \qquad (20)$$

Finally, set $\beta = 22.5°$, $\zeta = 0$, and $\eta = 22.5°$. Then $$\Delta S/\sigma_0 = r_p r_s (\sin(\phi_p - \phi_\perp)) \approx r_p r_s \sin(\phi_p - \phi_s), \qquad (21)$$

from which the phase difference between $r^{(p)}$ and $r^{(s)}$ can be obtained. The same experiment can be performed without the $\lambda/4$ plate, in which case the sine in Eq.(21) will be replaced by cosine. Another possibility is to let $\beta = 22.5°$ and $\zeta = 45°$. In this case Eq. (18) becomes $$-\Delta S/\sigma_0 = r_\perp{}^2 \sin 4\eta + r_p r_s \sin(\phi_p - \phi_s - 4\eta) - r_p r_\perp$$
$$\sin(\phi_p - \phi_\perp - 4\eta) - r_s r_\perp$$
$$\sin(\phi_s - \phi_\perp + 4\eta) \approx r_p r_s \sin(\phi_p - \phi_s - 4\eta). \qquad (22)$$

$\eta$ can now be adjusted for maximum or minimum signal. It can also be set to 22.5° for the same result as one would obtain without the $\lambda/4$ plate.

Experiment 2: Set $\beta = 0°$ and $\zeta = 45°$. Then $$\Delta S/\sigma_0 = 2 r_p r_\perp \sin(\phi_p - \phi_\perp - 4\eta). \qquad (23)$$

Since this is a small signal, its direct measurement is subject to various errors in the system. Fortunately, it is possible to reverse the sign of $r_\perp$ by switching the magnet and measure the difference in $\Delta S$. This would yield $$\delta/\sigma_o = \frac{\Delta S\uparrow - \Delta S\downarrow}{\sigma_o} = 4 r_p r_\perp \sin(\phi_p - \phi_\perp - 4\eta) \qquad (24)$$

By measuring $\delta/\sigma_0$ at $\eta = 0°$ and $\eta = 22.5°$, we obtain both the amplitude product $r_p r_\perp$ and the phase difference $\phi_p - \phi_\perp$.

Experiment 3: Similar to Experiment 2 but with the incident polarization being s instead of p. Thus $\beta = 45°$, $\zeta = 45°$, and $$\delta/\sigma_o = \frac{\Delta S\uparrow - \Delta S\downarrow}{\sigma_o} = 4 r_s r_\perp \sin(\phi_s - \phi_\perp + 4\eta) \qquad (25)$$

which is identical to Eq. (24) for s-polarized incident light. The importance of magnetization reversal is clear from these two experiments as the measurement of $r_\perp$ is routine, given appropriate choices for the angles $\beta$ and $\zeta$.

EXAMPLE 1

Figure 4A:
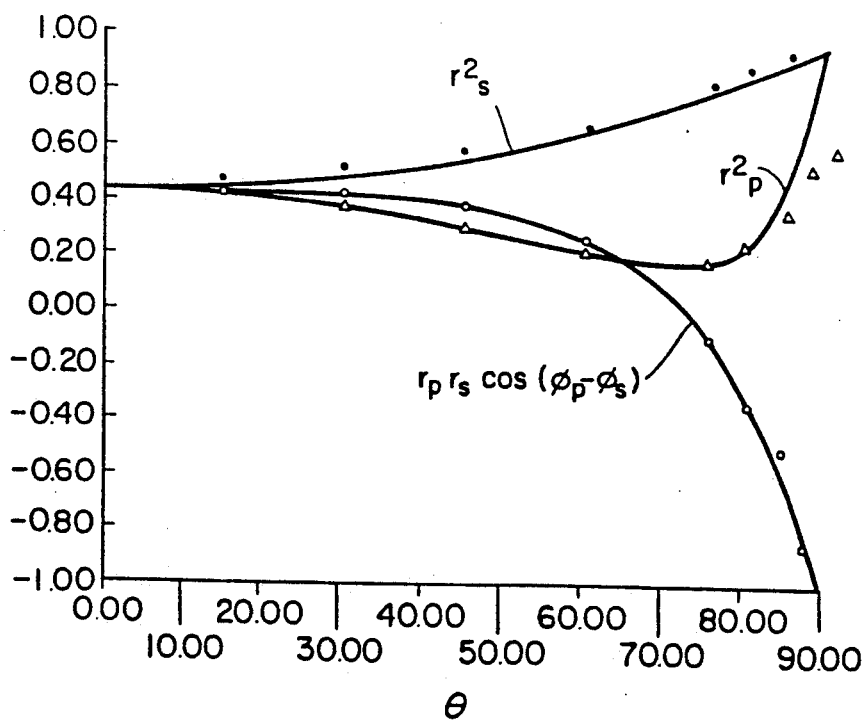
FIGS. 4(a)-4(c) are graphical comparisons of theoretical and experimental values of reflection coefficients and the indicated expressions for $Tb_{28} Fe_{72}$.

The results of reflectivity measurements on a $Tb_{28}Fe_{72}$ sample are presented in FIG. 4. The sample was sputter deposited on a quartz substrate and in situ overcoated with a 300 Å layer of silicon dioxide. The thickness of the TbFe layer is approximately 1000 Å, which, for all practical purposes is optically thick.

The three sets of data correspond to the three experiments discussed above. The solid curves are theoretical results obtained for $e_x = e_x = -2.6 + i(20)$, which is the same value obtained by Connell et al. See G. A. N. Connell and D. S. Bloomberg "Amorphous Rare Earth Transition Metal Alloys," Mott Festschrift, Plenum, N.Y., 1985. Connell's results are for TbFe samples deposited under similar conditions. Connell's measurements, however, were performed at normal incidence, and did not provide information on the value of $e_z$. The good match between theory and experiment here suggests that the assumption $e_x = e_z$ for these samples is not a bad assumption, although structural anisotropy in the perpendicular direction is known to occur in samples deposited under other conditions (such as high argon pressure). Also, the presence of cobalt in an alloy is usually accompanied by columnar growth in the perpendicular direction. In such situations, our method is capable of providing information about the existence and strength of the structural anisotropy.

Figure 4B:
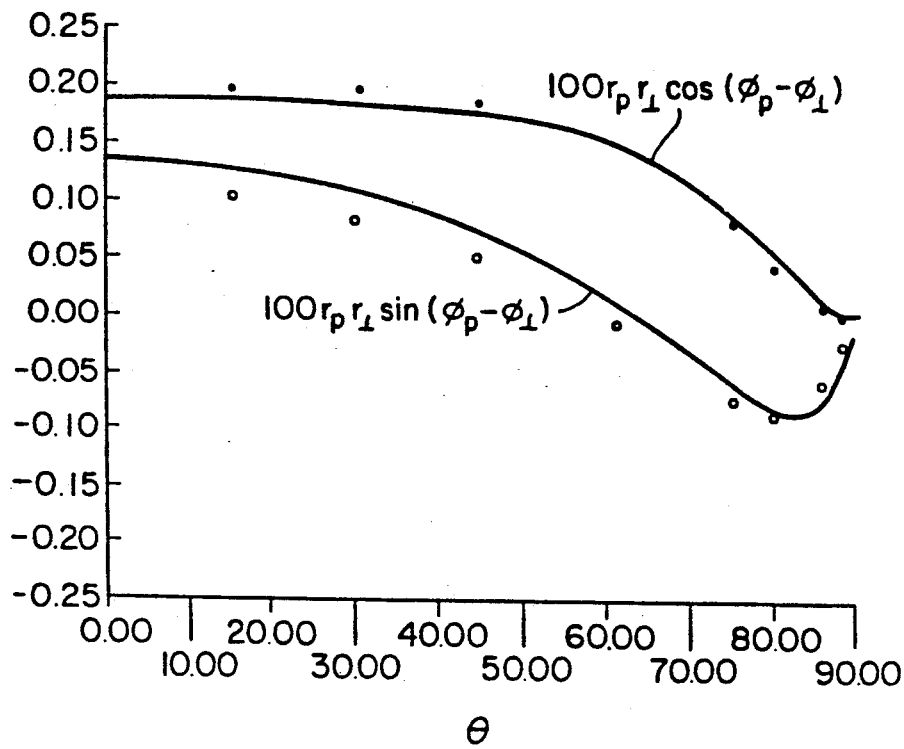

FIG. 4b shows the results of experiment 2. The data represent reflection coefficients plotted versus the angle of incidence, and the solid curves are obtained from theoretical calculations using $e_{xy} = -0.04 + i(o.33)$. This is Connell's value for $e_{xy}$.

Figure 4C:
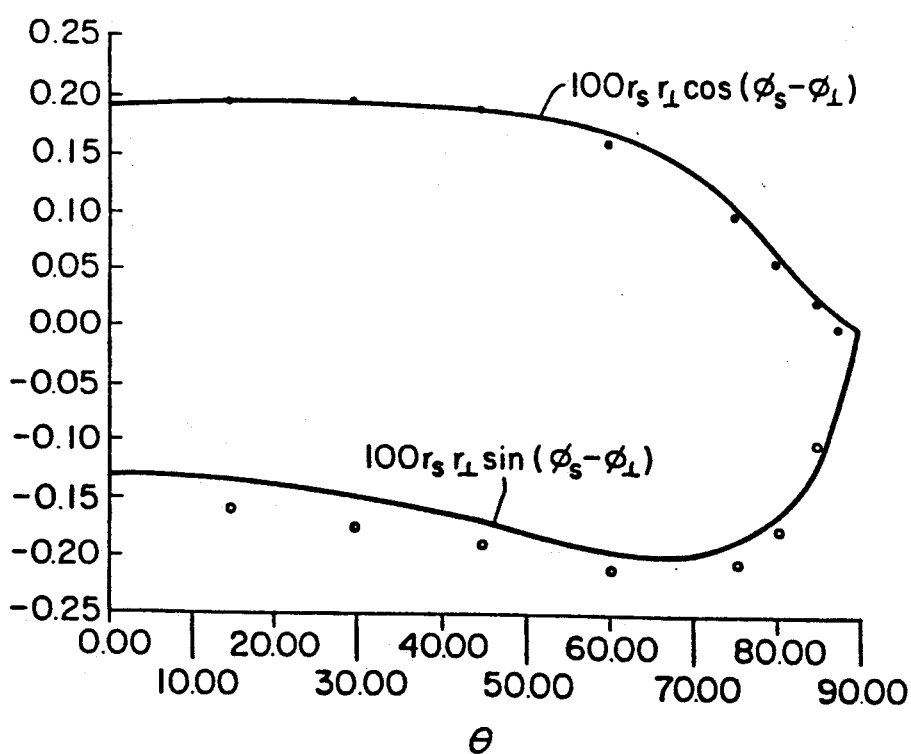

FIG. 4c corresponds to the third experiment, and the data shown here are the indicated functions plotted versus $\theta$. The values $e_x$, $e_z$, and $e_{xy}$ are the same as above. The general behavior and numerical value of the results are in good agreement. Discrepencies at 85° and above are attributed to the spreading of the incident beam on the film surface at large angles of incidence. The beam spot becomes larger than the constant field region of the magnet, and undergoes distortion on leaving the hemispherical lens because some rays are not reflected from the center of curvature.

EXAMPLE 2

Figure 5A:
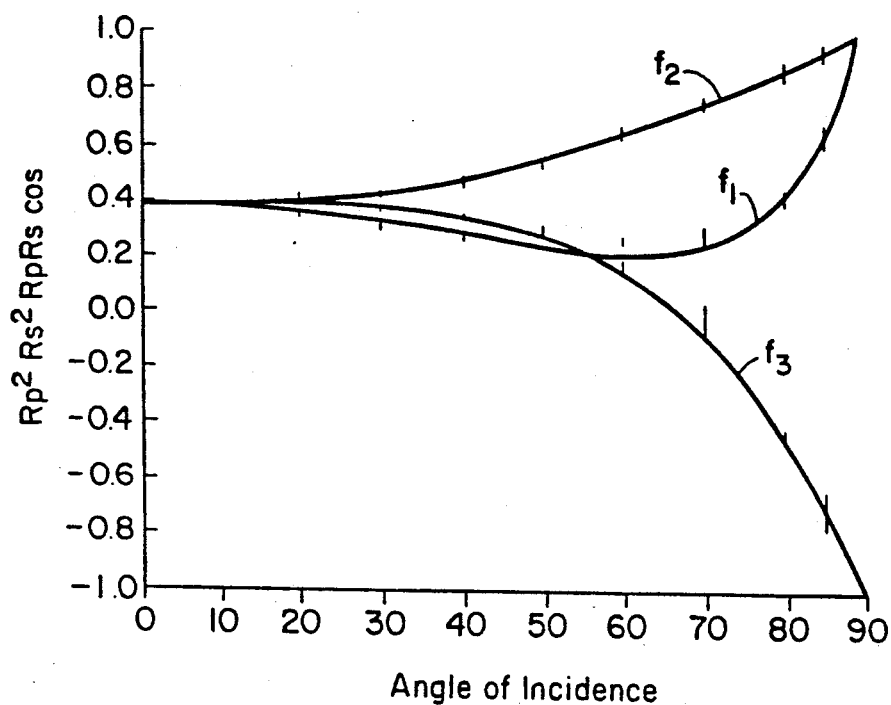
Figure 5B:
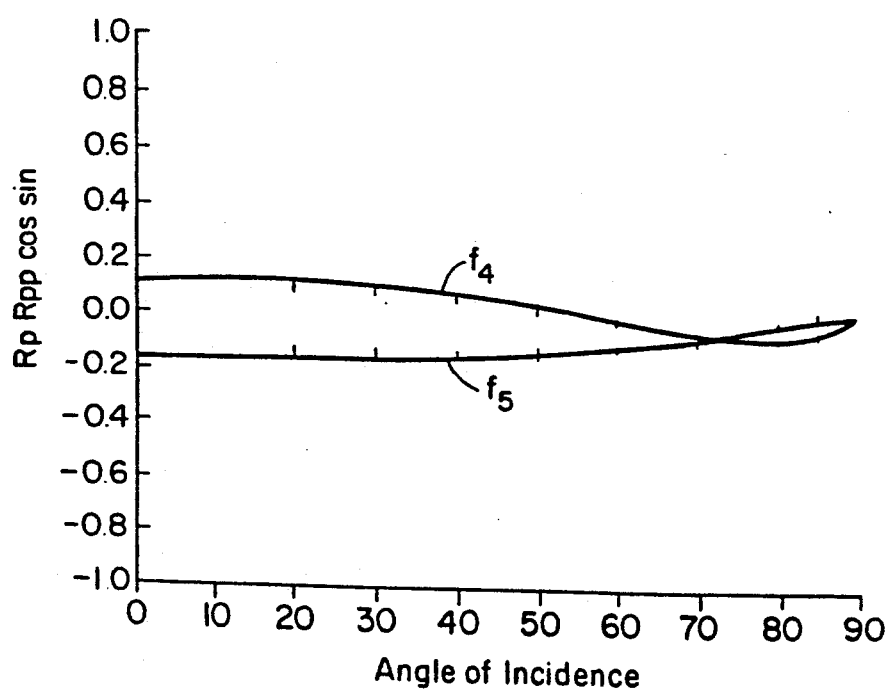

FIG. 5 compares theoretically estimated curves with averaged data from four experiments. The designated functions are plotted versus the angle of incidence $\theta$. One standard deviation ranges over the four experiments are shown as error bars at each angle. The functions $f_1$, $f_2$, $f_3$, $f_4$, $f_5$, $f_6$ and $f_7$ are defined in Table 1:

TABLE I

| | |
|---|---|
| $f_1$ | $r_{p2}{}^2$ |
| $f_2$ | $r_s$ |
| $f_3$ | $r_p r_s \cos(\phi_p - \phi_s)$ |
| $f_4$ | $r_p r_\perp \sin(\phi_p - \phi_\perp)$ |
| $f_5$ | $r_p r_\perp \cos(\phi_p - \phi_\perp)$ |
| $f_6$ | $r_s r_\perp \sin(\phi_s - \phi_\perp)$ |
| $f_7$ | $r_s r_\perp \cos(\phi_s - \phi_\perp)$ |

The sample with composition $(Tb_{17.9}Fe_{82.1})AR_{11.8}$ had a TbFe layer of 2000 Å with 500 Å of $Al_2O_3$ as overcoat. Observations were taken over a period of a month, starting about two months after the sample was deposited. Each column of Table II shows estimates from one experiment, while the last column represents estimates based on the averages of the observations, in an attempt to eliminate the effects of random experimental variability. The variability in estimates is due to variations in the data, especially at higher angles of incidence. Variability across the four experiments of ±5% was common at angles above 70° for almost every function measured.

TABLE II

| ESTIMATE | 1 | 2 | 3 | 4 | AVG Data |
|---|---|---|---|---|---|
| $Re(e_x)$ | −2.91 | −2.55 | −3.09 | −2.82 | −2.91 |
| $Im(e_x)$ | 9.49 | 12.50 | 9.11 | 9.76 | 10.10 |
| $Re(e_{xy})$ | −0.067 | −0.065 | −0.064 | −0.066 | −0.068 |
| $Im(e_{xy})$ | 0.104 | 0.156 | 0.152 | 0.113 | 0.115 |
| Fig. Merit × $10^3$ | 6.52 | 6.78 | 6.58 | 6.72 | 6.59 |

The figure of merit is given by the right-hand side of the expression:

$$r_\perp \leq \frac{|e_{xy}|}{2\, Im(e_x)}$$

This expression provides an upper bound on the ratio of useful magneto-optical signal to incident laser power available from the medium. Thus, $r_\perp$ is a measure of the usefulness of materials for erasable memory systems.

The estimates from the averaged data for $e_x(-2.91+i10.1)$ and $e_{XY}(-0.068+i0.115)$ are comparable to published values for TbFe films of similar composition. The figure of merit for the sample is $6.59 \times 10^{-3}$. The estimates were used to recreate the observations in FIG. 5. Discrete symbols show the averaged observations for each function and the solid lines are the predicted reflectivity curves using the estimated dielectric tensor values.

The estimated dielectric tensor elements were obtained through the use of the multivariate gradient algorithm of Levenberg-Marquardt. See K. M. Brown and J. E. Dennis, *Numerische Mathematik* 18: 289 (1972).

While the invention has been particularly shown and described with reference to preferred embodiments thereof, it will be understood by those skilled in the art that various changes in form and details may be made without departing from the spirit and scope of the invention as defined in the appended claims.

We claim:

1. A method of measuring reflectivity comprising:
    illuminating a magnetooptic material with polarized light having a selected orientation;
    reflecting the light from the surface of said material;
    measuring a first intensity of the light reflected by said material;
    applying a magnetic field to the magnetooptic material to produce a direction of magnetization in the material;
    measuring a second intensity of light reflected from the magnetized material; and
    determining a complex reflection coefficient from the first and second measured intensities.

2. A method of measuring reflectivity as defined in claim 1 further comprising the steps of:
    reversing the direction of magnetization of the material; and
    measuring the intensity of the light reflected from the reversely magnetized material in two orthogonal planes.

3. A method of reflectivity as defined in claim 1 wherein said illuminating step is preceded by the steps of:
    forming a transparent protective layer on the magnetooptic material; and
    positioning a lens on said layer such that light normally incident upon said lens is essentially not reflected or refracted by the lens or the protective layer.

4. A method of measuring reflectivity as defined in claim 3 wherein film is placed between the lens and said protective layer having the same refractive index as said lens and layer.

5. A method of measuring reflectivity as defined in claim 3 further comprising the step of normalizing the measured intensity by measuring the intensity of light that is internally reflected by the lens without the layer and material.

6. A method of measuring reflectivity as defined in claim 1 wherein said magnetooptic material is illuminated from any of a multiplicity of angles.

7. A method of measuring reflectivity as defined in claim 1 wherein said illuminating step is preceded by the step of rotating the polarization of said light.

8. A method of measuring reflectivity as defined in claim 7 wherein said rotating step is comprised of rotating a polarizing beam splitter.

9. A method of measuring reflectivity as defined in claim 8 further comprising the step of normalizing the measured intensity by measuring variations in a polarized light source signal split by the beam splitter.

10. A method of measuring reflectivity as defined in claim 1 wherein said reflecting step is followed by the step of adjusting the phase delay of the reflected light.

11. A method of measuring reflectivity as defined in claim 1 wherein said reflecting step is followed by the step of rotating the polarization of the reflected light.

12. A method of measuring reflectivity as defined in claim 11 wherein said rotating step is comprised of rotating a polarizing beam splitter.

13. Apparatus for measuring reflectivity of magnetooptic material comprising:
    a polarized light source;
    a magnetooptic material illuminated by said source;
    a magnetic field source positioned adjacent the material to provide a selected direction of magnetization to the material;
    a moveable device to modify a phase difference between orthogonal components of light reflected by the material; and
    a detector system to measure the orthogonal components of reflected light by the material, the system having means to determine a complex reflection coefficient a complex reflection coefficient of the material from the measured orthogonal components.

14. The apparatus of claim 13 further comprising a hemispheric lens positioned between the light source and the magnetooptic material to direct light from the source onto a surface of the material.

15. The apparatus of claim 14 wherein the lens and the surface are coupled by a film.

16. A method of measuring reflectivity comprising:
    illuminating a magnetooptic material with polarized light having a selected orientation;

reflecting the light from the surface of said material;

measuring a first intensity of the light reflected by said material;

applying a magnetic field to the magnetooptic material to produce a direction of magnetization in the material;

modifying a phase difference between orthogonal components of light reflected by the material;

measuring a second intensity of light reflected from the magnetized material; and determining a complex reflection coefficient from the first and second measured intensities.

* * * * *

UNITED STATES PATENT AND TRADEMARK OFFICE
CERTIFICATE OF CORRECTION

PATENT NO.  : 5,108,185

DATED       : April 28, 1992

INVENTOR(S) : Masud Mansuripur, Michael Ruane, Robert Rosenvold and Amit Jain

It is certified that error appears in the above-identified patent and that said Letters Patent is hereby corrected as shown below:

Title page, item (75):
 Please add Amit Jain as a named inventor.

Signed and Sealed this

Nineteenth Day of October, 1993

Attest:

BRUCE LEHMAN

Attesting Officer             Commissioner of Patents and Trademarks